United States Defensive Publication [19] (H) [11] T977,008

Di Sanzo et al. [43] Dec. 5, 1978

[54] CONTROL OF NEMATODES WITH SELECTED N-AMINOSULFENYL, N-ARYLSULFENYL AND N-ACYL-AMIDOSULFENYL DERIVATIVES OF 2,3-DIHYDRO-2,2-DIMETHYL-7-BENSOFURANYL METHYLCARBAMATE

[75] Inventors: Carmine P. Di Sanzo; John F. Engel, both of Medina, N.Y.

[73] Assignee: FMC Corporation, Philadelphia, Pa.

[21] Appl. No.: 890,543

[22] Filed: Mar. 20, 1978

Related U.S. Application Data

[63] Continuation of Ser. No. 739,218, Nov. 5, 1976, abandoned.

[51] Int. Cl.[2] ..... A01N 9/28; A01N 9/00; A01N 9/22

[52] U.S. Cl. ..... 424/285; 424/244; 424/248.52; 424/250; 424/263; 424/267; 424/268

[57] ABSTRACT

A method is disclosed for the control of nematodes which comprises applying to the situs of infestation certain N-aminosulfenyl carbamates of the formula

I

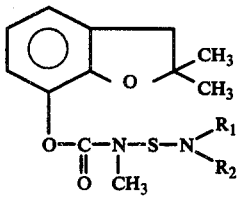

N-arylsulfenyl carbamates of the formula

II

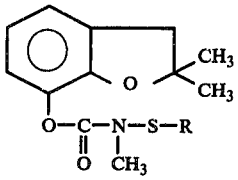

or N-acylamidosulfenyl carbamates of the formula

III

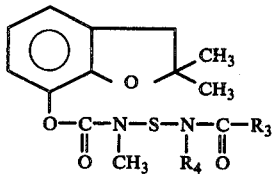

wherein $R_1$ and $R_2$ are each independently selected from straight or branched chain alkyl or alkoxyalkyl having 1 to 8 carbon atoms, cycloalkyl having 3 to 7 carbon atoms, phenyl, halophenyl, phenyl(lower)alkyl, halophenyl(lower)alkyl and loweralkoxybenzyl; and wherein $R_1$ and $R_2$ may be taken together with the nitrogen to form an optionally substituted heterocyclic ring of 5 to 8 members which may contain one additional hetero atom consisting of oxygen, sulfur, or nitrogen; R is

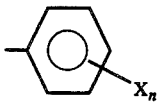

wherein each X is independently selected from halogen and lower alkyl, and *n* is an integer of 0 to 5 inclusive; and $R_3$ is hydrogen or lower alkyl and $R_4$ is straight or branched chain alkyl having 1 to 7 carbon atoms, cycloalkyl having 3 to 7 carbon atoms, phenyl, or benzyl; and wherein $R_3$ and $R_4$ may be taken together with the carbonyl and the nitrogen to form an optionally substituted heterocyclic ring of 5 to 8 members, which may contain one additional hetero atom selected from oxygen, nitrogen, and sulfur.

17 Claims, No Sheets Drawing,

48 Pages Specification

The file of this unexamined application may be inspected and copies thereof may be purchased (849 O.G. 1221, Apr. 9, 1968).